US005097826A

United States Patent [19]

Gray et al.

[11] Patent Number: 5,097,826

[45] Date of Patent: Mar. 24, 1992

[54] PRESSURE MONITORING DEVICE FOR SELF-CONTAINED BREATHING APPARATUS

[75] Inventors: Robert E. Gray, Glen Mills; Robert M. Armstrong, Clifton; Gene Keohane, Philadelphia, all of Pa.; Christopher E. Coombs, Boonton Township, Morris County, N.J.

[73] Assignee: Cairns & Brother, Inc., Clifton, N.J.

[21] Appl. No.: 436,255

[22] Filed: Nov. 13, 1989

[51] Int. Cl.[5] .......... A61M 16/00

[52] U.S. Cl. .......... 128/204.18; 128/205.23; 128/202.22; 128/204.26

[58] Field of Search .......... 128/202.22, 204.21, 128/205.23, 204.18, 204.26; 340/705; 73/714

[56] References Cited

U.S. PATENT DOCUMENTS

| | | | |
|---|---|---|---|
| 3,584,596 | 6/1971 | Westcott | 128/202.22 |
| 3,712,714 | 1/1973 | Uyeda et al. | 340/705 |
| 3,957,044 | 5/1976 | Fletcher et al. | 128/202.22 |
| 4,187,842 | 2/1980 | Schreiber | 238/202.22 |
| 4,192,001 | 3/1980 | Villa | 128/204.23 |
| 4,387,600 | 6/1983 | Kranz | 73/714 |
| 4,498,471 | 2/1985 | Kranz et al. | 128/202.22 |
| 4,658,358 | 4/1987 | Leach et al. | 128/204.23 |
| 4,882,678 | 11/1989 | Hollis et al. | 128/204.23 |
| 4,905,683 | 3/1990 | Cronjaeger | 128/202.22 |
| 4,949,072 | 8/1990 | Comerford et al. | 340/705 |

*Primary Examiner*—Edgar S. Burr
*Assistant Examiner*—Aaron J. Lewis
*Attorney, Agent, or Firm*—Louis E. Marn

[57] ABSTRACT

There is disclosed a pressure monitoring device for self-containing breathing apparatus including visual indicators disposed in the field of view from the head-piece to monitor when predetermine pressure levels are reached in the tank which supplies gas to that head-piece. The predetermined pressure levels are referenced to the residual tank pressure at which the required breathing gas flow is not sustained and visual alarm provisions anticipate those predetermined pressure levels which are critical, in some embodiments of the invention. A cost effective transducer of reduced pressure range senses the tank pressure and noise is eliminated from the transducer signal by common mode rejection in still other embodiments.

17 Claims, 4 Drawing Sheets

PRESSURE MONITORING DEVICE FOR SELF-CONTAINED BREATHING APPARATUS

BACKGROUND OF THE INVENTION

1. Field of the Invention

This invention relates generally to the monitoring of gas supply pressure in self-contained breathing equipment and more particularly, to such monitoring which is continuously within view, readily discernible, cost effective directly related to flow sustaining pressure.

2. Description of the Prior Art

Self-contained breathing apparatus (or SCBA) is commonly worn in contaminated or irrespirable environments. Some activities in which such environments are encountered include underwater reconnaissance and firefighting. SCBA equipment generally includes a facepiece which includes a lens for external viewing and is supplied with breathing gas from a pressurized cylinder or tank, through a hose. The tank is secured to a person's body by a harness and its pressure is monitored to inform the person regarding its remaining capacity. Such monitoring was traditionally accomplished with a gauge in which a Bourdon tube rotates a pointer about a dial as pressure changes. However, electronic gauges with digital readouts of tank pressure in psi and gauges with fiberoptic displays as disclosed in U.S. Pat. No. 4,387,600 are now available. All of these gauges are disposed on the SCBA equipment at remote locations from the field of view through the lens of the facepiece and are often forgotten or ignored by those wearing such equipment. Furthermore, when these gauges are utilized, the person wearing the equipment must totally divert their visual and mental attention to view the gauge. In typical equipment, the gauge is disposed at the end of a pressurized hose which clips to the harness in the chest region and must be unclipped, then extended from the chest and properly positioned for reading.

Other disadvantages are also encountered with these gauges. Electronic gauges with a digital readout require a mental interpretation to correlate current pressure with full cylinder capacity and time in use to determine same. Also, these gauges include no visual alarm provisions for indicating when critically low pressure levels are reached (although audible warning devices are commonly used and required by regulation). The cost of most electronic gauges is greatly elevated by a pressure transducer which must be accurate over a wide pressure range, typically 4500 psi.

OBJECTS OF THE PRESENT INVENTION

These and other objects of the present invention are to permit a person wearing SCBA equipment to observe the tank pressure gauge readings without diverting either their visual or mental attention, or interrupting their physical activities.

An object of the present invention is to provide a SCBA tank pressure gauge in accordance with the above stated general object wherein pressure indications are referenced to the full tank pressure.

Another object of the present invention is to provide a SCBA tank pressure gauge in accordance with the above stated general object wherein visual alarm provisions are included to warn that critical pressure levels are approaching, or to indicate to the wearer that it is his apparatus which has a low pressure condition when he may be among several other apparatus with audible low pressure alarms.

Yet another object of the present invention is to provide a SCBA tank pressure gauge in accordance with the above stated general object wherein the cost of the pressure transducer is lowered by reducing the pressure range to be monitored thereby.

Still another object of the present invention is to provide a SCBA tank pressure gauge in accordance with the above stated general object wherein inaccuracies due to electrical noise are avoided through the use of common mode rejection circuitry.

SUMMARY OF THE INVENTION

These and other objects are accomplished by sensing the tank pressure with an electrical transducer from which a signal is directed to signal comparators that individually detect each predetermined pressure level to be monitored, while light emitting diodes (hereinafter referred to as LED's) are disposed in the field of view from the facepiece, which are separately controlled by the individual comparators to indicate when the predetermined pressure levels are reached. To reference the LED pressure indications to the residual tank pressure, a voltage divider is connected to set the predetermined pressure levels with a precisely fixed voltage being applied in combination therewith to set the lowest predetermined pressure level. The LED indicator relating to at least one critical predetermined pressure level is controlled through a relaxation oscillator as an anticipatory warning regarding those levels. To decrease the pressure range and, thus, the cost of the electrical transducer, a pressure reducer is combined therewith through a liquid interface and the transducer signal is passed through an amplifier which includes a differential input arrangement to cancel out the common mode or noise in the signal.

BRIEF DESCRIPTION OF THE DRAWING

The scope of the present invention is only limited by the appended claims for which support is predicated on the preferred embodiments hereinafter set forth in the following description and the attached drawings wherein like reference characters relate to like parts throughout the figures.

DETAILED DESCRIPTION OF THE INVENTION

Figure 1:
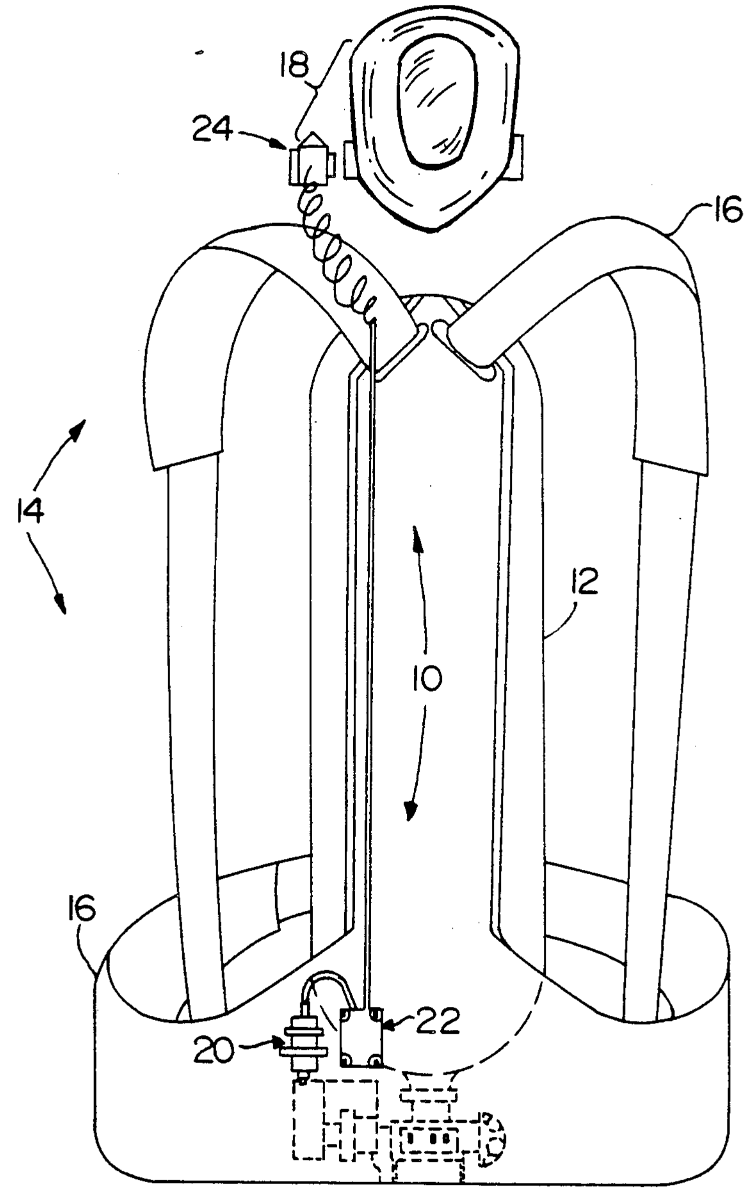
FIG. 1 is an overall view of commonly used SCBA equipment with the present invention incorporated therein.
Figure 2:
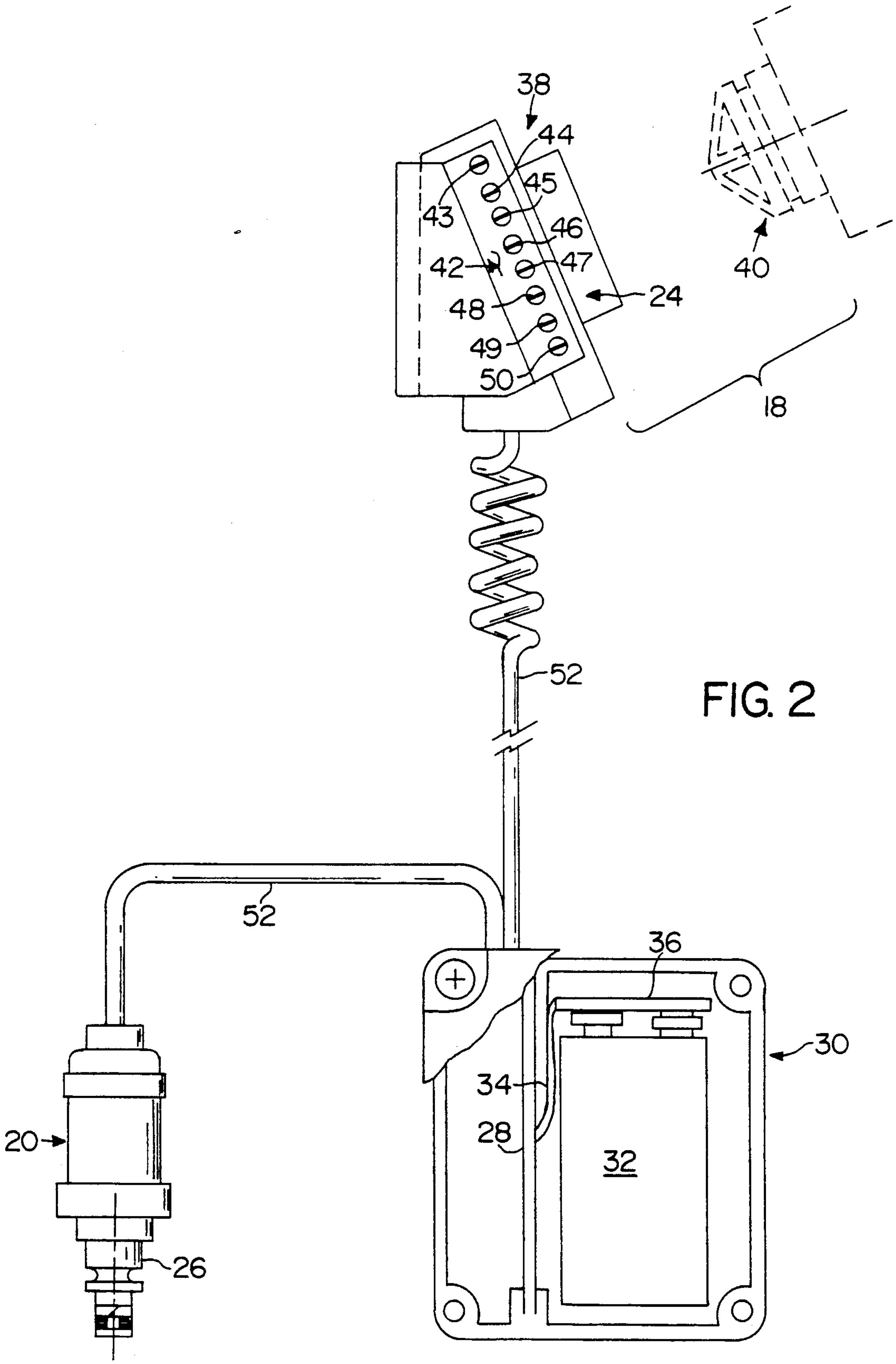
FIG. 2 is a layout view showing the distribution of the major components in the preferred embodiments of the present invention.

Referring now to the drawing, there is illustrated a pressure monitoring apparatus, generally indicated as 10 for monitoring at least one predetermined pressure level within a tank 12 which supplies breathing gas in SCBA equipment 14. As shown in FIG. 1, the equipment 14 also includes a harness 16 to which the tank 12 is secured and a facepiece or headpiece 18 to which the breathing gas is supplied from the tank 12 through a hose 39. General distribution for the component parts of the apparatus 10 is shown in FIG. 1 and specific details regarding such parts are provided in FIG. 2. In this distribution, an electrical transducer means 20 senses the pressure in the tank 12 and a circuit means 22 detects when the pressure sensed by the transducer means 20 reaches each predetermined pressure level, while an illuminated means 24 in the field of view from the headpiece 18 indicates when each predetermined level is reached.

Of course, any electrical pressure transducer having a pressure range compatible with that of the tank 12 could be utilized for the transducer means 20. However, a connective interface between the tank 12 and the transducer means 20 must be provided and therefore, the transducer means 20 is contained within a conventional tank fitting 26. The circuit means 22 is disposed on either a printed or integrated circuit board 28, along with other circuitry. This circuit board 28 is contained within an electronics module 30, along with a battery 32, wires 34 and electrical connectors 36. A gas supply interconnect is provided to the headpiece 18 and includes a female fitting 38 to which the hose 39 from the tank 12 attaches and a male fitting 40 on the headpiece 18. The illumination means 24 is disposed on at least one surface 42 of the female fitting 38 which becomes located in the field of view from the headpiece 18 when the gas supply interconnect is made. For the preferred embodiments of the invention disclosed herein, the illumination means 24 includes individual LED's 43, 44, 45, 46, 47, 48, 49 and 50 which each indicate when a predetermined pressure level is reached. Furthermore, the electronics module 30 is electrically interconnected to the transducer means 20 and the female fitting 38 through wires (not shown) in a cable 52. Those of ordinary skill in the art of SCBA equipment will understand without any further explanation that the scope of this invention is not limited by the number of LED's utilized in the illumination means 24. Artisans will also understand that the hose from the tank 12 could be attached directly to the headpiece 18, such as is commonly the case in SCBA equipment for use in underwater environments.

Figure 3:
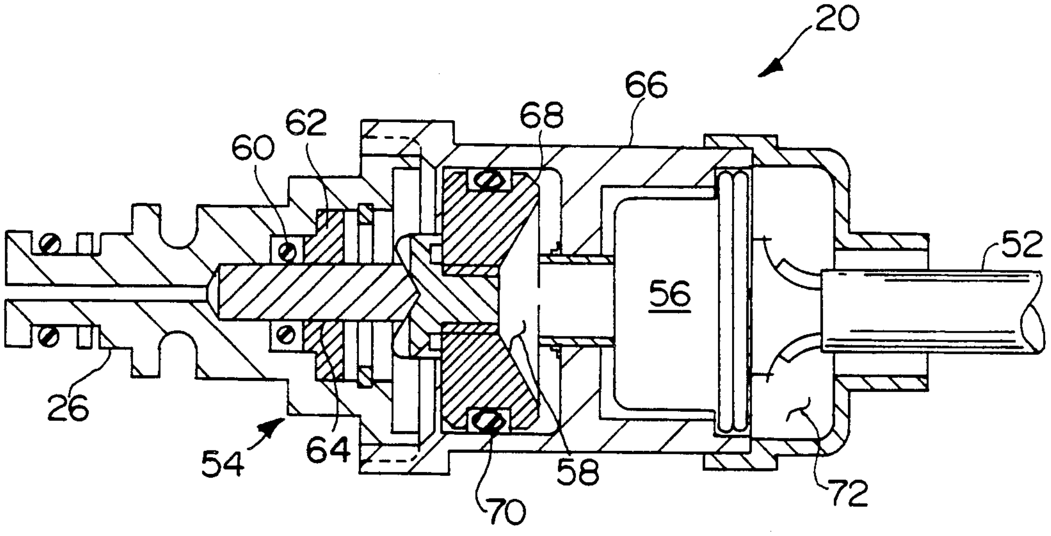
FIG. 3 is a cross-sectional view of the pressure reducer/transducer combination found in some embodiments of the present invention.

Because a maximum pressure of 4500 psi is common for the tank 12 and the cost of electrical pressure transducers with such a high range is excessive, the transducer means 20 in some preferred embodiments of the invention includes a reducer 54 which applies the tank pressure to an electrical transducer 56 through a liquid interface 58, as shown in FIG. 3. Consequently, the required pressure range of the transducer 56 decreases in accordance with the stepdown pressure ratio of the reducer 54 and of course, the cost of the transducer 56 decreases with its range. Tank fitting 26 is modified with an o-ring 60 and bushing 62 to guide the longitudinal movement of a cylindrical rod 64, while applying the tank pressure at one circular end thereof. A housing assembly 66 interconnects with the tank fitting 26 and guides the longitudinal movement of a cylindrical piston 68 in one end chamber thereof, while the transducer 56 is retained in the other end chamber thereof. The liquid interface 58 passes through an opening between the end chambers of the housing assembly 66 and at least one o-ring 70 precludes the leakage of liquid past the piston 68, while the wires in the cable 52 are connected to pins on the transducer 56 before it is hermetically sealed into the housing assembly 66, such as with epoxy 72.

When the fitting 26 is inserted in a high pressure housing 21 to which the tank 12 is connected, the pressure therein is applied across the circular end of the rod 64 and a longitudinal force develops therein. The magnitude of this force is equal to the circular end area of the rod 64 multiplied by the tank pressure and it is transferred directly to the piston 68 which develops a pressure across the circular end area thereof. The magnitude of this pressure is equal to the magnitude of the force divided by the circular end area of the piston 68 and is transferred to the transducer 56 through the liquid interface 58. Because the end area of the rod 64 is less than the end area of the piston 68, the reducer 54 steps the tank pressure down at the transducer 56 with the stepdown ratio being equal to the end area of the rod 64 divided by the end area of the piston 68. Therefore, if the stepdown ratio is 1/20, the transducer 56 need only have a range of 0 to 225 psi to sense the pressure of a tank 12 having a range of 0 to 4500 psi.

Figure 4:
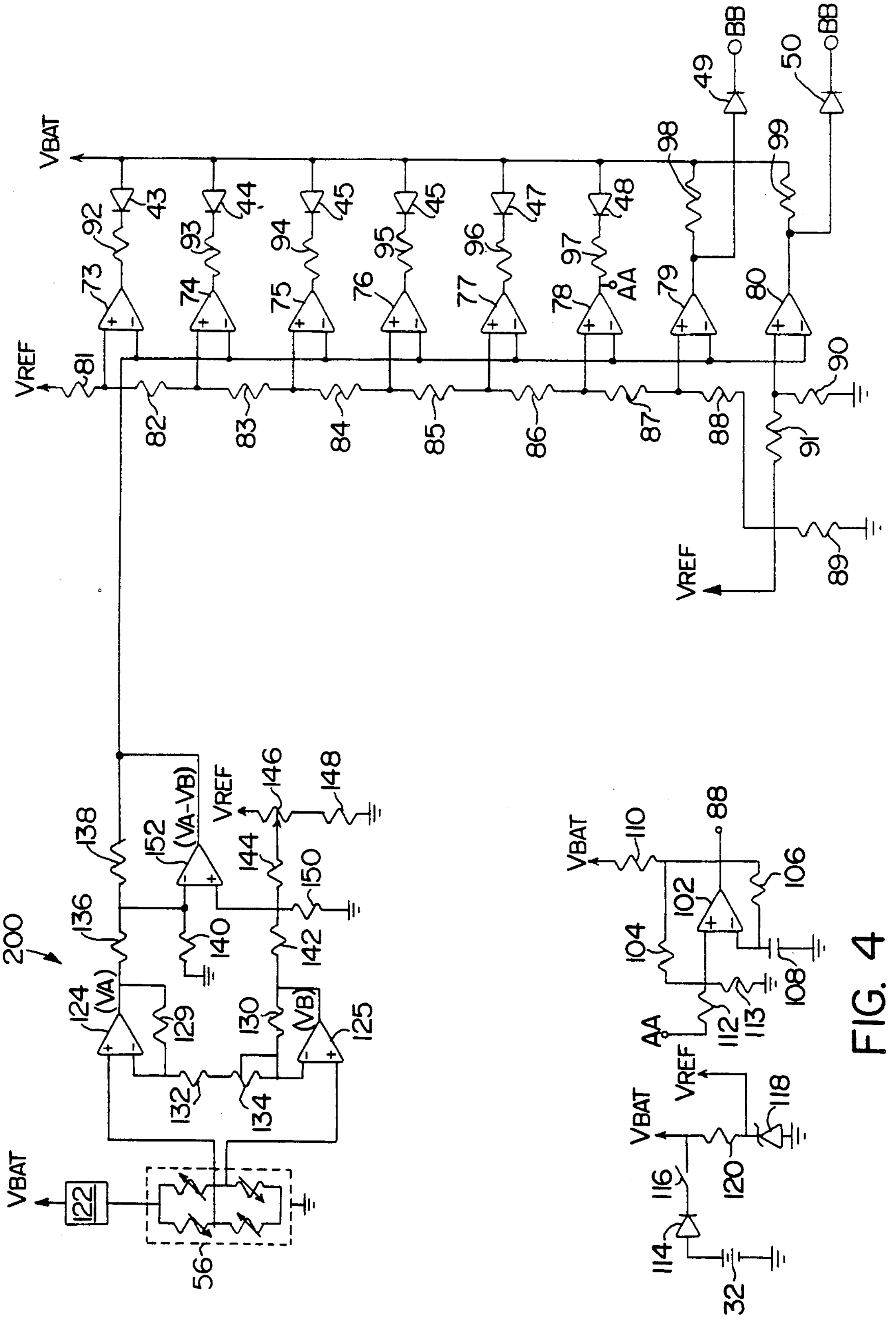
FIG. 4 is a schematic diagram for the circuitry utilized in the preferred embodiments of the present invention.

FIG. 4 illustrates one of the circuit implementations which are possible for use in the apparatus 10 of the present invention, the pressure indicator is supplied with a voltage from a sufficiently sized battery 32 and a reference voltage ($V_{REF}$) developed across zener diode 118. The power is applied through switch 116. The electronics consists of a pressure transducer 56 of the strain gauge type. In this application the pressure transducer must be supplied with a constant current source 122. The output of the pressure transducer feeds an instrumentation amplifier 200. The amplifier is made up of two sections, the buffer, op amp 124 and 126, and a differential amplifier, op amp 152. The pressure transducer is tied to both noninverting inputs of op amps 124 and 126, and appear as very high impedances. The inverting sides of the op amps 124 & 126 are tied to a balanced feedback network consisting of resistors 128, 130, 132, and 134. Resistor 134, of this network, is a variable resistor which provides a span adjustment, which sets the full tank pressure. The output of op amp 124 (VA) and the output of op amp 126 (VB) are one to one to the inputs but because of the high input inpedance the signals are relatively noise free. The output of op amp 124 is tied to the inverting input of op amp 152 through resistor 136 and the output of op amp 126 is tied through resistor 142. The remaining resistors tied to op amp 152 create a relative balance between inputs so that the output of op amp 152 is equivalent to VA-VB. In the resistor network tied to op amp 152 a variable resistor 146 is provided for a zero adjust referenced to $V_{REF}$. This would be the empty bottle setting. The output of op amp 152 is tied to the inverting inputs of op amps 73 through 78 and the noninverting inputs of op amp 79 and 80. The noninverting inputs of op amps 73 through 78 and the inverting inputs of op amps 79 and 80 are tied to the divider network, made of resistors 81 through 90, at resistively different points.

Those predetermined valves create the trip points for the LED drivers, op amps 73 through 80, and represent amounts of bottle pressure used. In a full bottle situation all op amps have a low output which biases all LEDs on. As bottle pressure decreases a predetermined voltage level change is felt on each op amp. As each op amp output is progressively changed from low to high the LEDs are biased off. When op amp 78 output goes high it is also applied to a relaxation oscillator made up of op amp 102, resistors 104 through 113 and capacitor 108. As a high is presented on the noninverting input of op amp 102 the output goes high. This output is tied to the cathode of LEDs 49 and 50. This biases the LEDs 49 and 50 off until capacitor 108, tied to the inverting input of op amp 102, charges sufficiently and flops the output low, which then biases LEDs 49 and 50 on again. This creates a flashing or visual alarm of a critically low bottle pressure situation. All alarm levels, except for the last, are ratiometric and can be divided up differently for each application. However, the last alarm point, in this application, is an absolute valve, hence the inverting input of op amp 80 is tied to $V_{REF}$ through resistor 91. This allows the last alarm point to be other than zero bottle pressure. Also any number of LED drivers can be configured as op amps 79 and 80 to create more flashing LEDs.

Those skilled in the art of SCBA equipment will appreciate without any further explanation that within the concept of this invention, many modifications and variations are possible to the above disclosed embodiments of pressure monitoring apparatus for such equipment. Therefore, it should be understood that all such modifications and variations fall within the scope of the following claims.

What is claimed is:

1. Breathing apparatus, comprising: a facepiece proving a field of view to a wearer thereof, said facepiece provided with a first fitting;

a tank for containing pressurized breathing gas;

a hose including a first end for being connected to said tank and a second end provided with a second fitting for being connected to said first fitting to supply breathing gas through said hose to said wearer of said facepiece;

illumination means for being illuminated to indicate the presence of a predetermined pressure level of said breathing gas in said tank, said illumination means mounted on said second fitting in a predetermined position to place said illumination means in said field of view of said wearer of said facepiece upon aid second fitting being connected to said first fitting; and monitoring means for monitoring the pressure level of said breathing gas in said tank and for illuminating said illumination means upon the pressure level of said breathing gas in said tank reaching said predetermined level.

2. The self-contained breathing apparatus as defined in claim 1 wherein said monitoring means are for monitoring a plurality of predetermined pressure levels within said tank and which monitoring means include an electrical transducer for deriving a signal in proportion to the pressure level in said tank; wherein said monitoring means include a plurality of individual signal comparators and wherein each individual signal comparator is for detecting when said transducer signal reaches one of said predetermined pressure levels; wherein said illumination means includes a plurality of individual light emitting diodes and wherein each individual light emitting diode is for indicating when one of said predetermined pressure levels is detected by said comparators.

3. The self-contained breathing apparatus as defined in claim 2 wherein said monitoring means includes a transducer and a pressure reducer connected to said transducer through a liquid interface and wherein the pressure within said tank is applied to said transducer through said liquid interface by said pressure reducer.

4. The self-contained breathing apparatus as define din claim 3 wherein said liquid interface is cylindrically configured and said reducer includes a cylindrical rod and a cylindrical piston, said rod being positionable in the tank with the pressure therein applied across a circular end thereof and being arranged to translate longitudinal force therein to longitudinal force in said piston, said liquid interface having pressure applied across one circular end thereof by one circular end of said piston and translating that pressure to said transducer through the other circular end thereof, with the pressure step-down ratio accomplished by said reducer being equal to the circular end area of said rod divided by the circular end area of said piston.

5. The self-contained breathing apparatus as defined in claim 2 wherein each said comparator is arranged to change from a signal to low level signal at an output terminal thereof when the voltage level at an input terminal thereof exceeds the voltage level at a threshold set terminal thereof.

6. The self-contained breathing apparatus as defined in claim 2 wherein the respective nodes of a voltage divider are individually connected to said threshold set terminals of said comparators.

7. The self-contained breathing apparatus as defined in claim 6 wherein the voltage drops between adjacent nodes on said voltage divider are of equal magnitudes.

8. The self-contained breathing apparatus as defined in claim 6 wherein a supplemental bias voltage is applied at the lowest level node on said voltage divider to offset the predetermined pressure level established thereby in accordance with the residual tank pressure at which the minimum required gas flow therefrom becomes unavailable.

9. The self-contained breathing apparatus as defined in claim 2 wherein all of said light emitting diodes are illuminated at maximum tank pressure, with each light emitting diode being shut off when the tank pressure drops to the predetermined pressure level indicated thereby.

10. The self-contained breathing apparatus as defined in claim 2 wherein two different colors of illumination are used to distinguish between acceptable and unacceptable pressure levels.

11. The self-contained breathing apparatus as defined in claim 2 wherein at least the lowest predetermined pressure level is indicated by a red light emitting diode.

12. The self-contained breathing apparatus as defined in claim 2 wherein at least the light emitting diode that indicates the lowest predetermined pressure level is shut off intermittently through a relaxation oscillator when a capacity alarm signal is applied through a voltage divider to the non-inverting input of an operational amplifier therein, said operational amplifier having separate feedback resistors connected from its output to its inverting and non-inverting inputs, with its inverting input being grounded through a capacitor, while a bias voltage is applied to its output through a resistor.

13. The self-contained breathing apparatus as defined in claim 12 wherein said capacity alarm signal is derived from one of said comparators when it detects a predetermined pressure level higher than the predetermined pressure level indicated by the light emitting diodes which are alternately shut off.

14. The self-contained breathing apparatus as defined in claim 2 wherein said transducer signal passes to said comparators through a differential amplifier means for rejecting common mode signals.

15. The self-contained breathing apparatus as defined in claim 14 wherein said differential amplifier means includes an output voltage amplifier and a pair of input voltage amplifiers, each of said voltage amplifiers including an operational amplifier with a feedback resistor connected between its output and inverting input, said input voltage amplifiers having said transducer signal applied across their non-inverting inputs and a resistor connected across their inverting inputs, said output voltage amplifier having its output applied to said comparators while its inverting and non-inverting inputs have the outputs from said input voltage amplifiers separately applied thereto through individual resistors and its non-inverting input biased through a voltage divider.

16. The self-contained breathing apparatus as defined in claim 15 wherein said resistor connected across the inverting inputs of said input voltage amplifiers is a variable resistor to provide for variable gain amplification of said transducer signal.

17. The self-contained breathing apparatus as defined in claim 15 wherein the non-inverting input of said output voltage amplifier is biased to ground through a variable resistor in a potentiometer arrangement to set the pressure signal from said differential amplifier means at the level desired to represent full tank pressure.

* * * * *